United States Patent
Scarpellini et al.

(10) Patent No.: US 9,522,172 B2
(45) Date of Patent: Dec. 20, 2016

(54) GM-CSF FOR USE IN THE PREVENTION OF SPONTANEOUS ABORTION AND EMBRYO IMPLANTATION FAILURE

(71) Applicants: Fabio Scarpellini, Rome (IT); Marco Sbracia, Rome (IT)

(72) Inventors: Fabio Scarpellini, Rome (IT); Marco Sbracia, Rome (IT)

(*) Notice: Subject to any disclaimer, the term of this patent is extended or adjusted under 35 U.S.C. 154(b) by 0 days.

(21) Appl. No.: 14/648,020

(22) PCT Filed: Dec. 3, 2013

(86) PCT No.: PCT/IB2013/002688
§ 371 (c)(1),
(2) Date: May 28, 2015

(87) PCT Pub. No.: WO2014/087218
PCT Pub. Date: Jun. 12, 2014

(65) Prior Publication Data
US 2015/0306180 A1  Oct. 29, 2015

(30) Foreign Application Priority Data
Dec. 3, 2012 (IT) ............................. MI2012A2063

(51) Int. Cl.
*A61K 38/19* (2006.01)

(52) U.S. Cl.
CPC .................. *A61K 38/193* (2013.01)

(58) Field of Classification Search
None
See application file for complete search history.

(56) References Cited

U.S. PATENT DOCUMENTS

2005/0272636 A1* 12/2005 Robertson .............. A61K 38/08
424/133.1

FOREIGN PATENT DOCUMENTS

| AU | WO9967364 | * 12/1999 | ............... C12N 5/08 |
|---|---|---|---|
| WO | 2004026333 | 4/2004 | |
| WO | 2010126528 | 11/2010 | |
| WO | 2010126553 | 11/2010 | |

OTHER PUBLICATIONS

Scarpellini et al., Fertility and Sterility, 2003; 80: S288.*
The abstract by Mai, Shengzhi Yixue Zazhi. 2013; 22(4): 266-270.*
Information downloaded from Medical Subject Headings (MeSH) on Jul. 13, 2016 (ncbi.nlm.nih.gov/mesh/2010046; 2 pages total) regarding Filgrastim (i.e., granulocyte colony stimulating factor); 2 pages total.*
Hill, American Journal of Reproductiove Immunology, 1992; 28: 123-128.*
Chaouat et al., J Reprod Fert. 1990; 89: 447-458.*
Sjoblom et al., Human Reproduction, 1999; 14: 3069-3076.*
Clark, et al., Prevention of Spontaneous Abortion in DBA/2-Mated CBA/J mice by GM-CSF Involves CD8 <+> T Cell-Dependent Suppression of Natural Effector Cell Cytotoxicity against Trophoblast Target Cells:, Cellular Immunology, vol. 154, No. 1, Mar. 1, 1994, pp. 143-152.
Aagaard-Tillery, et al., "Immunology of Normal Pregnancy", Seminars in Fetal and Neonatal Medicine, vol. 11, No. 5, Oct. 1, 2006, pp. 279-295.
Mori, et al., "Immunomolecular Mechanism in Mammalian Implantation", Endocrine Journal, vol. 41, no. Suppl., Jan. 1, 1994, pp. S17-S31.
Matthiesen, et al., "Multiple Pregnancy Failures: An Immunological Paradigm", American Journal of Reproductive Immunology, vol. 67, No. 4, Apr. 1, 2012 pp. 334-340.
Perricone, et al., "GM-CSF and Pregnancy: Evidence of Significantly Reduced Blood Concentrations in Unexplained Recurrent Abortion Efficiently Reverted by Intravenous Immunoglobulin Treatment", American Journal of Reproductive Immunology, vol. 50, No. 3, Sep. 1, 2003, pp. 232-237.
Anonymous: "Introduction Embryogen—The First Documented IVF Medium with Natural Growth Factor", Nov. 4, 2011.
International Search Report of PCT/IB2013/002688 of Apr. 30, 2014.

* cited by examiner

*Primary Examiner* — Christina Borgeest
(74) *Attorney, Agent, or Firm* — Silvia Salvadori, P.C.; Silvia Salvadori

(57) ABSTRACT

The invention relates to GM-CSF for use in a method for the prevention of spontaneous abortion in a subject suffering from recurrent miscarriage, comprising administering to said subject an effective amount of GM-CSF as sole active substance, wherein said method also prevents or reduces the likelihood of embryo implantation failure in the subject undergoing an assisted reproduction procedure.

7 Claims, 2 Drawing Sheets

GM-CSF FOR USE IN THE PREVENTION OF SPONTANEOUS ABORTION AND EMBRYO IMPLANTATION FAILURE

This application is a U.S. national stage of PCT/IB2013002688 filed on 3 Dec. 2013, which claims priority to and the benefit of Italian Application No. MI2012A002063, filed on 3 Dec. 2012, the contents of which are incorporated herein by reference in their entireties.

FIELD OF APPLICATION

The present invention relates to the use of GM-CSF (Granulocyte Macrophage-Colony Stimulating Factor) in the prevention of spontaneous abortion and embryo implantation failure.

PRIOR ART

GM-CSF (Granulocyte Macrophage-Colony Stimulating Factor) is a protein secreted by different cell strains including macrophages, T lymphocytes, mastocytes, NK cells, endothelial cells and fibroblasts.

GM-CSF is a cytokine which performs the function of a white blood cell growth factor. GM-CSF stimulates the growth of stem cells and the differentiation of stem cells into granulocytes (neutrophils, eosinophils and basophils) and into monocytes. The monocytes which exit the circulatory system and penetrate into the tissues develop and mature into macrophages and dendritic cells. Therefore GM-CSF is a component of the immuno-inflammatory cascade system which, by means of activation of a small number of macrophages, rapidly leads to a substantial increase in the number of these activated cells, this being a crucial process for combating infections. The active form of this protein is present extracellularly as a homodimer. In its mature biological form, the human Granulocyte Macrophage-Colony Stimulating Factor is a glycosylated protein.

The gene of GM-CSF has been localized in human beings in a cluster of related genes on the long arm of the chromosome 5 in the region 5q31, recognized as being associated with the chromosome deletion that produces the 5q-syndrome and acute myelogenous leukemia. The genes of this cluster also encode the interleukins 4, 5 and 13.

This growth factor performs its function by bonding to a specific receptor thereof present on the surface of the target cells, the Granulocyte Macrophage-Colony Stimulating Factor receptor, also known as CD116 (Cluster of Differentiation 116). The receptor for the GM-CSF is located on the white blood cells, promoting the growth thereof, as well as on the stem cells, myeloblasts and neutrophils, but not on the erythroid cells and megacaryocytes. Moreover this receptor is associated with the surfactant metabolism dysfunction type 4.

This receptor is a heterodimer composed of at least two different subunits, alpha chain and beta chain, the latter also being present in the receptor of IL-3 and IL-5. The alpha subunit contains a specific site for the GM-CSF binding, while the beta subunit is involved in signal transduction.

Association of the alpha and beta subunits results in functional activation of the receptor. Upon dimerization of the two subunits, alpha and beta, the latter is phosphorylated on a tyrosine residue by a kinase, a phosphorylating enzyme of the Janus kinase (JAK) family. This results in an association of the receptor with a Shc protein, or adaptor protein. This protein interacts with the GRB2/SoS complex, which activates a whole series of molecules in the post-receptor pathway which leads to nuclear activation of the cell.

GM-CSF is also known as molgramostim or, when the protein is produced by yeast cells, as sargramostim (Leukine); these molecules have a pharmacological use.

GM-CSF is used as a drug for stimulating the production of white blood cells in patients who have undergone oncological chemotherapy.

GM-CSF is also used and is currently being evaluated in controlled studies for its potential as a vaccine adjuvant in HIV-infected patients.

The preliminary studies have been particularly encouraging, but the American Food and Drug Administration (FDA) has not yet approved use of GM-CSF for this purpose.

Leukine is the registered trade name of sargramostim, recombinant GM-CSF produced by yeast cells, developed by Immunex (now Amgen), administered for the first time in 1987, as part of a compassionate-use protocol, to six men who were victims of radioactive cesium contamination following the accident which occurred in Goiania. It is currently produced by Berlex Laboratories, a subsidiary of Schering AG. Its use is currently approved both in the USA and in Europe for treatment following autologous bone marrow transplantation in patients with myeloproliferative pathologies such as non-Hodgkin's lymphoma, acute lymphocytic leukemia or Hodgkin's disease. Moreover, in 1996 the FDA approved the use of sargramostim for the treatment of fungal infections and the treatment of post-chemotherapy aplastic anemia.

Recently Berlex, the pharmaceutical company producing GM-CSF, funded a study which was published in 2005 in the New England Journal of Medicine and which concluded that GM-CSF promotes a significant increase in remissions in patients suffering from Crohn's disease with a reduction in the severity of the illness and improvement in the quality of life, even though this data has not been confirmed by other studies.

Moreover recently GM-CSF has been tested for the treatment of patients suffering from Alzheimer's disease, for demyelinating diseases such as multiple sclerosis, for treatment and revascularization in myocardial infarction and for the treatment of cerebral thrombosis, with encouraging results. In these cases the capacity of GM-CSF to stimulate the growth of stem cells, and in particular those which regenerate the endothelial cells, has been advantageously employed.

In 1999 it was also shown how GM-CSF added to the culture medium for mice embryos promoted their development to blastocysts.

It was also proposed using culture media to which GM-CSF (Granulocyte-macrophage colony stimulating factor) was added in order to favour the development of human embryos in vitro (C. Sjöblom et al., "Granulocyte-macrophage colony-stimulating factor promotes human blastocyst development in vitro", Human Reproduction vol. 14, No. 12, pp 3069-3076, 1999).

Patent application WO 2005/539505 refers to a method for preventing spontaneous abortion, comprising the administration of an effective amount of G-CSF. The application in question refers also to a method for preventing implantation failure during assisted reproduction, comprising the administration of an effective amount of G-CSF.

Patent application WO 2010/126528 describes a method for preventing or reducing the probability of implantation failure in a subject undergoing artificial insemination, comprising the administration of an effective amount of a composition containing G-CSF. This application mentions the possibility that this composition may comprise an additive, including GM-CSF among the numerous additives mentioned, but it does not attribute any particular function to it.

Patent application WO 2010/126553 refers to a method for reducing the probability of implantation failure or spontaneous abortion in a subject undergoing an assisted reproduction procedure selected from among FET, ICSI, GIFT or ZIFT, comprising the administration of an effective amount of a composition containing G-CSF. This application mentions the possibility that this composition may comprise an additive, including GM-CSF among the numerous additives mentioned, but it does not attribute any particular function to it.

Patent application WO 2004/026333 describes the treatment of recurrent miscarriage and spontaneous abortion by means of administration of an effective amount of a compound which inhibits the activity of IFN-y, such as a TGF-β, and the possible additional administration of GM-CSF.

Clark D. A. et al. "Prevention of spontaneous abortion in DBA/2-mated CBA/J mice by GM-CSF involves CD8+ T cell-dependent suppression of natural effector cell cytotoxicity against trophoblast target cells", Cellular Immunology 154, 143-152 (1994), describes a model of mouse spontaneous abortion and the prevention of spontaneous abortion by administration of GM-CSF.

Aagaard-Tillery et al., "Immunology of normal pregnancy", Seminars in fetal and neonatal medicine, Elsevier, GB, vol. 11, No. 5, 1 Oct. 2006, pages 279-295, describe the administration of GM-CSF to a murine model of spontaneous abortion, which results in a reduction of pregnancy loss and an increase in the placental and fetal weight.

Mori T et al., "Immunomolecular mechanisms in mammalian implantation", Endocrine Journal, Tokyo, JP, vol. 41, Suppl. No. 1 January 1994, pages S17-S31, describes the administration of GM-CSF to prevent spontaneous abortion in mice. This article states that, in the murine model CBA/J DBA/2 of spontaneous abortion, the administration of GM-CSF increased the placental and fetal weight, but was unable to reduce the incidence of fetal resorption in the pregnant mice which were spontaneous abortion prone.

Leif Matthiesen et al. "Multiple pregnancy failures: an immunological paradigm", American Journal of Reproductive Immunology, vol. 67, No. 4, 1 Apr. 2012, pages 334-340, describes the use of GM-CSF for treatment of recurrent spontaneous abortion. In this article it is reported that GM-CSF was launched to be used in the settings of in vitro fertilization (IVF) because it improves apposition, adhesion, differentiation and invasion of the embryo.

Perricone R. et al., "GM-CSF and pregnancy: evidence of significantly reduced blood concentrations in unexplained recurrent abortion efficiently reverted by intravenous immunoglobulin treatment", American Journal of Reproductive Immunology, vol. 50, No. 3, 2003-09-01, pages 232-237, reports that women with unexplained recurrent miscarriage show reduced blood concentrations of GM-CSF and that intravenous treatment with immunoglobulins efficiently reverses this situation, resulting in near doubling of the GM-CSF concentrations.

Since 1997 the research group of the Applicants has been carrying out various clinical and laboratory studies into the use of G-CSF (Granulocyte Colony Stimulating Factor), a hormone of the CSF family, to which GM-CSF and M-CSF (Macrophage-Colony Stimulating Factor) also belong, in the treatment of recurrent miscarriage, repeated implantation failure and development of the embryo in vitro.

With reference to the aforementioned studies, the Applicants have directed their research efforts towards developing a new method for preventing recurrent miscarriage and repeated embryo implantation failure, which might show unexpected results compared to the known methods.

Therefore the object of the present invention is to provide a method for preventing spontaneous abortion in patients with a history of recurrent miscarriage, where "recurrent miscarriage" is understood as meaning at least three miscarriages, and for preventing or reducing the likelihood of spontaneous abortion or implantation failure in the aforementioned subjects, when undergoing assisted reproduction procedures.

SUMMARY OF THE INVENTION

In order to achieve this object, the present invention provides GM-CSF for use in a method for the prevention of spontaneous abortion in a subject suffering from recurrent miscarriage, which comprises administering to said subject an effective amount of GM-CSF as the sole active substance, wherein said method prevents or also reduces the likelihood of embryo implantation failure in the aforementioned subject when undergoing an assisted reproduction procedure.

GM-CSF is preferably administered parenterally, conveniently subcutaneously. The daily administered dose is preferably 0.1 to 100 mcg/kg, conveniently 0.5 to 10 mcg/kg and advantageously about 1 mcg/kg.

GM-CSF, when used for the method described above, is administered every day from the day of ovulation to the ninth week of pregnancy.

The aforementioned assisted reproduction procedure may be any one from among those commonly used in medical practice, such as ICSI (intracytoplasmic sperm injection), GIFT (gamete intrafallopian transfer), ZIFT (zygote intrafallopian transfer) and FET (frozen embryo transfer).

GM-CSF is used in the pharmaceutical forms which are commercially available, namely in the form of a lyophilized powder intended to be reconstituted by means of the addition of water for injectable solutions and containing any excipients suitable to ensure the stability of the protein GM-CSF, favour the solubilization thereof and ensure the isotonicity of the reconstituted solution. An example of a GM-CSF formulation which can be used for the present invention consists of the product marketed by Novartis under the trade name Leucomax®.

As will emerge from the examples provided in the description below, with the GM-CSF used in the aforementioned method it has been possible to obtain results which were entirely unexpected in the light of the known methods of the prior art and achieve a substantial reduction in the spontaneous abortion rate in subjects suffering from recurrent miscarriage as well as pregnancy and embryo implantation rates higher than those achieved hitherto with the methods according to the prior art.

DETAILED DESCRIPTION OF A PREFERRED EMBODIMENT

Further features and advantages of the present invention will become clear from the examples provided hereinbelow by way of illustration and not of limitation.

Example 1

This experiment was intended to study the use of GM-CSF or Molgramostim (trade name Leucomax) in the daily dose of 1 mcg/kg (about 60 mcg per day) in women suffering from recurrent miscarriage (at least three consecutive miscarriages) sine causa (without a cause which can be diagnosed by current diagnostic methods) in an attempt to prevent miscarriage in these women.

This treatment was compared with a control group of women suffering from the same pathology treated daily with 100 mg of intramuscular progesterone for the same period following ovulation.

The study included 30 women divided into two groups of 15 patients each, less than 38 years old, who suffered from recurrent miscarriage and had had at least 4 preceding consecutive miscarriages and in whom the last miscarriage had taken place during treatment with high doses of intravenous immunoglobulin where the karyotype of the aborted embryo was normal (46XX or 46XY).

15 of these women were treated daily with 1 mcg/kg of Molgramostim (Leucomax, Novartis), equivalent to a daily dose of about 60 mcg, subcutaneously, starting from the day of ovulation (diagnosed by means of ultrasound during monitoring of the menstrual cycle) until the day of the pregnancy test, i.e. 14 days after ovulation, and, if the test was positive, until the ninth week of pregnancy still with the same dose.

The other 15 women were treated daily with intramuscular progestins using the same procedures and for the same duration as the other group (Prontogest, IBSA, 100 mg per day). All 30 women were monitored in the same manner by means of ultrasound fortnightly as from the positive pregnancy test and with weekly plasmatic determination of the beta-HCG.

All the women remained pregnant within three months following the start of the study. The results showed that 12 out of the 15 women (80%) treated with GM-CSF (1 mcg/kg of Molgramostim per day) completed the pregnancy, while 6 out of the 15 women (40%) treated with "placebo", i.e. Prontogest, completed pregnancy (P=0.03).

Figure 1:
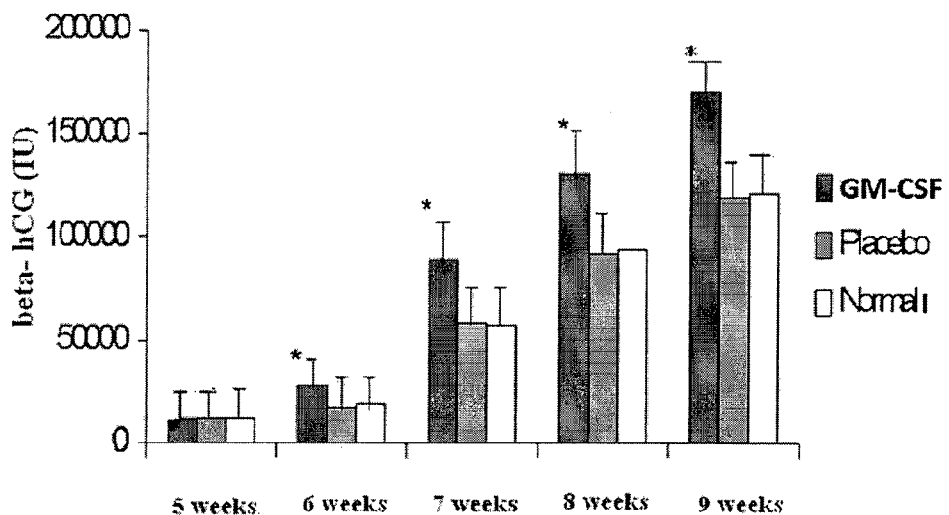
FIG. 1 is a diagrammatic representation of the results of experiments according to Example 1 reported in the description below.

Moreover, the beta-HCG values for the completed pregnancies in the two groups showed that these were much higher in the women treated with GM-CSF (see FIG. 1). The beta-HCG values of the women treated with GM-CSF, in addition to being higher than those recorded in the group treated with "placebo", were also higher than the beta-HCG values recorded for women who had non-pathological pregnancies without miscarriage (shown in the columns marked "Normal" in the graph of FIG. 1).

This experiment shows that GM-CSF is able to prevent in an effective and significant manner spontaneous abortion in female subjects suffering from sine causa recurrent miscarriage.

Example 2

This experiment was intended to study the use of GM-CSF or Molgramostim (trade name Leucomax) in a daily dose of 1 mcg/kg (about 60 mcg per day) in women suffering from repeated implantation failure following in vitro fertilization cycles (at least three attempts at assisted reproduction or ICSI cycles, with transfer into the uterus of at least 8 embryos of good morphological quality) sine causa (without a cause which can be diagnosed by current diagnostic methods) in an attempt to obtain pregnancy in these women. This treatment was compared with a control group of women suffering from the same pathology treated daily with 100 mg of intramuscular progesterone for the same period following in vitro fertilization.

The study included 30 women divided into two groups of 15 patients each, who suffered from repeated implantation failure following in vitro fertilization cycles as specified above. The first group of 15 women were treated daily with 1 mcg/kg of Molgramostim (Leucomax, Novartis) subcutaneously, equivalent to a daily dose of about 60 mcg, starting from the day prior to embryo transfer until the day of the pregnancy test, i.e. 14 days after transfer, and, if the test was positive, until the ninth week of pregnancy still with the same dose.

The 15 women of the second group were treated daily with intramuscular progestins using the same procedures and for the same duration as the other group (Prontogest, IBSA, 100 mg per day). All 30 women were monitored in the same manner by means of ultrasound fortnightly as from the positive pregnancy test and with weekly plasmatic determination of the beta-HCG.

Figure 2:
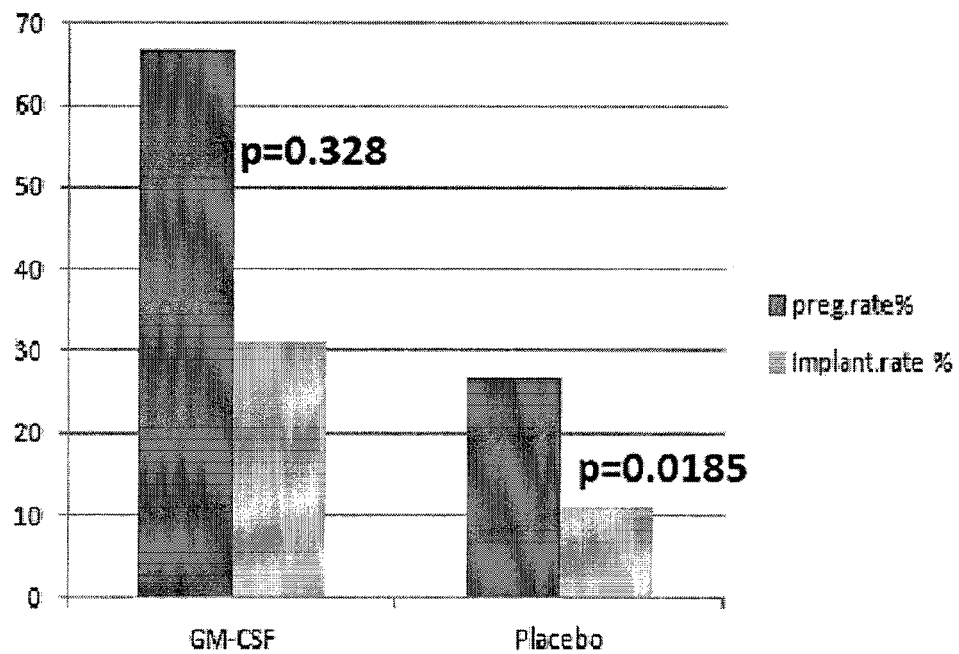
FIG. 2 is a diagrammatic representation of the results of experiments according to Example 2 reported in the description below.

The results, illustrated in the graph of FIG. 2, show that 10 out of the 15 women treated with GM-CSF (1 mcg/kg of Molgramostim per day) achieved pregnancy, equivalent to a pregnancy rate of 66.6.%, while 4 out of the 15 women treated with "placebo" (Prontogest) achieved pregnancy, equivalent to a pregnancy rate of 26.7% (P=0.0328).

Moreover, the implantation rate (i.e. the percentage of the embryos which were implanted and showed clinical signs such as a gestational sac revealed by ultrasound) in the women treated with GM-CSF was 31.1% as opposed to 11.1% (P=0.0185).

Example 3

This experiment was intended to study the use of GM-CSF or Molgramostim (trade name Leucomax) in a daily dose of 1 mcg/kg (about 60 mcg per day) on women suffering from repeated implantation failure following in vitro fertilization cycles (at least three attempts at assisted reproduction or ICSI cycles, with transfer into the uterus of at least 8 embryos of good morphological quality) sine causa (without a cause which can be diagnosed by current diagnostic methods) in an attempt to obtain pregnancy in these women. This treatment was compared with a control group of women suffering from the same pathology treated daily with 1 mcg/kg of G-CSF (Granulokine 30) for the same period following in vitro fertilization.

The study included 40 women divided into two groups of 20 patients each, who suffered from repeated implantation failure following in vitro fertilization cycles (at least three attempts at assisted reproduction or ICSI cycles, with transfer into the uterus of at least 8 embryos of good morphological quality). The 20 women of the first group were treated daily with 1 mcg/kg of Molgramostim (Leucomax, Novartis), equivalent to a daily dose of about 60 mcg, subcutaneously, starting from the day prior to embryo transfer until the day of the pregnancy test, i.e. 14 days after transfer, and, if the test was positive, until the ninth week of pregnancy still with the same dose.

The 20 women of the second group were treated daily with G-CSF (Granulokine 30) in a daily dose of 1 mcg/kg (about 60 mcg) using the same procedures and for the same duration as the other group. All 40 women were monitored in the same manner by means of ultrasound fortnightly as from the positive pregnancy test and with weekly plasmatic determination of the beta-HCG.

Figure 3:
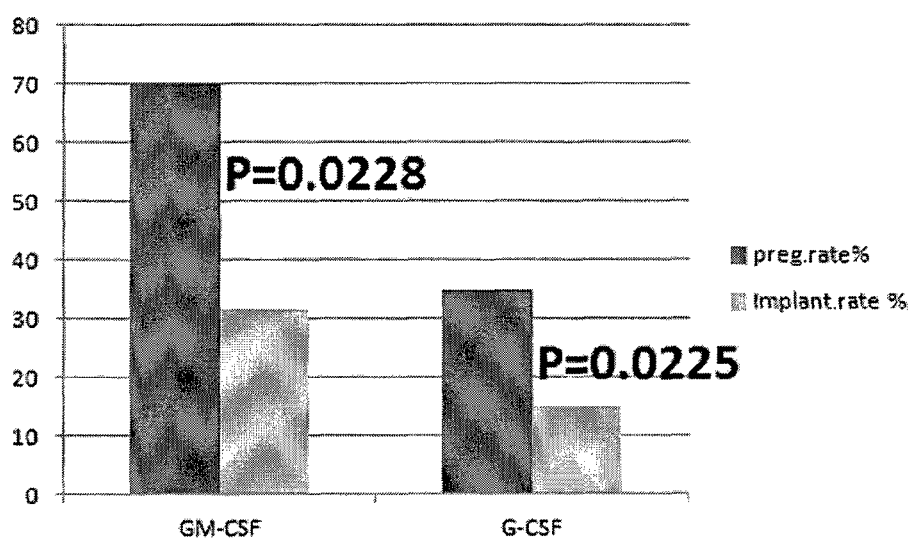
FIG. 3 is a diagrammatic representation of the results of experiments according to Example 3 reported in the description below.

The results, illustrated in the graph of FIG. 3, show that 14 out of the 20 women treated with GM-CSF (1 mcg/kg of Molgramostim per day) achieved pregnancy, equivalent to a pregnancy rate of 70.0%, while 7 out of the 20 women treated with G-CSF achieved pregnancy, corresponding to a pregnancy rate of 35.0% (P=0.028).

Moreover, the implantation rate (i.e. the percentage of the embryos which were implanted and showed clinical signs such as a gestational sac revealed by ultrasound) in the women treated with GM-CSF was 31.6% as opposed to 15.0% (P=0.0225).

The results of this experiment clearly showed the superiority of GM-CSF compared to G-CSF for the prevention or reduction of the likelihood of spontaneous abortion or implantation failure in subjects undergoing assisted reproduction procedures.

The invention claimed is:

1. A method of reducing the likelihood of spontaneous abortion in a subject suffering from recurrent miscarriage, or alternatively, a method of reducing the likelihood of implantation failure in a subject undergoing an assisted reproduction procedure, consisting of administering to said subject an effective amount of granulocyte macrophage-colony stimulating factor (GM-CSF), wherein the GM-CSF is administered every day at a dose of from 0.1 mcg/Kg to 100 mcg/Kg.

2. The method according to claim 1, wherein the GM-CSF is administered parenterally.

3. The method according to claim 1, wherein the GM-CSF is administered subcutaneously.

4. The method according to claim 1, wherein said daily administered dose is about 1 mcg/kg.

5. The method according to claim 1, wherein the GM-CSF is administered every day from the day of ovulation until the ninth week of pregnancy.

6. The method according to claim 1, wherein said assisted reproduction procedure is selected from the group consisting of intracytoplasmic sperm injection, gamete intrafallopian transfer, zygote intrafallopian transfer and frozen embryo transfer.

7. The method according to claim 1, wherein said daily dose is 0.5 mcg/kg to 10 mcg/kg.

* * * * *